Figure 1:
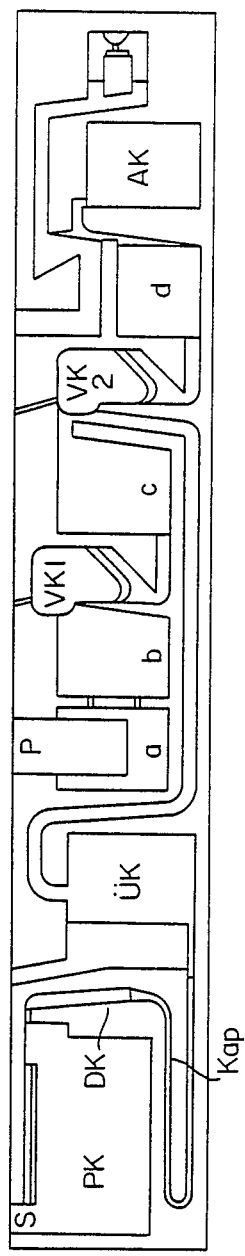

United States Patent [19]

Hübner-Parajsz et al.

[11] Patent Number: 4,762,783

[45] Date of Patent: Aug. 9, 1988

[54] PROCESS AND REAGENT FOR THE DETERMINATION OF THE FOLLICLE-STIMULATING HORMONE AND MONOCLONAL ANTIBODIES SUITABLE THEREFOR

[75] Inventors: Christa Hübner-Parajsz, Tutzing; Hartmut Schetters, Neufahrn; Helmut Lenz, Tutzing; Klaus Erler, Pöcking, all of Fed. Rep. of Germany

[73] Assignee: Boehringer Mannheim GmbH, Mannheim-Waldhof, Fed. Rep. of Germany

[21] Appl. No.: 834,316

[22] Filed: Feb. 27, 1986

[30] Foreign Application Priority Data

Mar. 6, 1985 [DE] Fed. Rep. of Germany ....... 3507849

[51] Int. Cl.$^4$ .................... G01N 33/532; C12N 15/00
[52] U.S. Cl. .......................................... 435/7; 435/68; 435/172.2; 435/240.27; 435/810; 435/948; 436/548; 436/808; 436/815; 530/387; 530/388; 935/106; 935/110; 935/99
[58] Field of Search .................... 435/7, 172.2, 172.3, 435/68, 240.27, 948, 810; 530/387, 388; 436/548, 808, 815; 935/106, 110, 99

[56] References Cited

PUBLICATIONS

Kofler et al–Chem. Abst., vol. 97 (1982) p. 213952b.
Hojo et al–Endocrinology, vol. 117, No. 6 (1985) pp. 2428–2434.

*Primary Examiner*—Sam Rosen
*Attorney, Agent, or Firm*—Felfe & Lynch

[57] ABSTRACT

The present invention provides an immunological process for the determination of the follicle-stimulating hormone (FSH), wherein there is used at least one monoclonal antibody which is directed specifically against FSH and cross-reacts with other glycoprotein hormones to an extent of less than 3%.

The present invention also provides a reagent for the determination of the follicle-stimulating hormone, wherein it contains at least one monoclonal antibody which is directed against FSH and cross-reacts with other glycoprotein hormones to an extent of less than 3%.

Furthermore, the present invention provides a monoclonal antibody against the follicle-stimulating hormone and a process and a hybridoma cell line for producing it.

32 Claims, 2 Drawing Sheets

PROCESS AND REAGENT FOR THE DETERMINATION OF THE FOLLICLE-STIMULATING HORMONE AND MONOCLONAL ANTIBODIES SUITABLE THEREFOR

The present invention is concerned with a process and reagent for the determination of the follicle-stimulating hormone, as well as with monoclonal antibodies suitable therefor.

The determination of the follicle-stimulating hormone (FSH) in body fluids, for example urine, serum and possibly also in plasma, is mainly used in order to be able to assess the endocrinological state of the hypothalamus, hypophysis and gonads. These investigations serve, in particular, for the differential diagnosis of hypogonadism, infertility and the like. In addition, the FSH determination is employed in order to determine the ovulation time point in the case of an induction of pregnancy.

In all these cases, the serum values lie within the physiological range. Furthermore, the concentration of FSH in the serum is also measured merely for the purpose of obtaining evidence regarding the biological effectiveness of this hormone. Therefore, a knowledge of the serum level of the native hormone is of diagnostic importance.

The physiological concentration of human FSH in the serum lies in the following ranges:

| | |
|---|---|
| men | 15 mIU/ml. |
| women before menopause, cycle | 10 mIU/ml. |
| women ovulation peak | 20–30 mIU/ml. |
| women after menopause | 30–80 mIU/ml. |

For the determination of FSH, immunological test processes are especially suitable in which the hormone is determined as antigen with one or more antibodies directed against it. The obtaining of antibodies with these polypeptide hormones involves difficulties since all polypeptide hormones are poorly immunogenic. Because of the homology between FSH and other glycoprotein hormones, for example the luteinising hormone (LH), thyreotropin-stimulating hormone (TSH) and human chlorionic gonadotropin (hCG), it is very difficult to obtain specific antibodies against one of these hormones. Usually, an antibody directed against one of these glycoprotein hormones shows more or less cross-reactivity with the other glycoproteins.

A monoclonal antibody which is directed specifically against FSH and shows no cross-reactivity with the other glycoprotein hormones is hitherto unknown. Therefore, at the moment, it is not possible to determine FSH immunologically without other glycoproteins being more or less co-determined.

It is an object of the present invention to provide a new immunological process and reagent with the help of which FSH can also be specifically determined in the presence of other glycoprotein hormones.

Thus, according to the present invention, there is provided an immunological process for the determination of the follicle-stimulating hormone (FSH), wherein there is used at least one monoclonal antibody which is directed specifically against FSH and cross-reacts with other glycoprotein hormones to an extent of less than 3%.

The present invention also provides a reagent for the determination of the follicle-stimulating hormone, wherein it contains at least one monoclonal antibody which is directed against FSH and cross-reacts with other glycoproteins to an extent of less than 3%.

As immunological determination methods, there can, in principle, be used all available immuno-assays, such as radio-immuno assay, enzyme-immuno assay, fluorescence-immuno assay and the like. Furthermore, all process variants, such as competitive immuno assay, sandwich process and the like can be used. For labelling, there can be used the agents which are conventional for the particular determination methods. Thus, in the case of a radio-immuno assay, radioisotopes, for example $^{125}I$, can be used for labelling. For an enzyme-immuno assay, there can be used all enzymes usually employed for this purpose, for example peroxidase or $\beta$-galactosidase. For a fluorescence-immuno assay, the usual fluorescing groups can be used as labels. Details of these various test methods and process variants are well known. Test variants are advantageous in which at least two monoclonal antibodies according to the present invention are employed which are directed against different antigenic determinants of FSH and at least one of which cross-reacts to an extent of less than 3% with other glycoprotein hormones.

For the determination of FSH, it has proved to be especially preferable to use the sandwich process in which the antigen to be determined is brought into contact with a carrier-bound and a labelled antibody. For such a determination process, a specific monoclonal antibody according to the present invention can, for example, be bound to the solid phase. This is incubated in a first incubation step with the sample which contains FSH to be determined, as well as, in general, other glycoprotein hormones, FSH thereby being selectively bound by the specific antibody. After the usual washing step, it is incubated with labelled antibody. This must not necessarily be directed specifically against FSH but can also cross-react with other glycoprotein hormones.

The process can also be carried out with a nonspecific, carrier-bound antibody. However, it is then necessary that, as labelled antibody, there is used an antibody according to the present invention which is directed specifically against FSH.

Variations of the sandwich process can also be used for the determination of FSH. Thus, for example, a soluble sandwich complex can first be formed with a non-labelled, soluble antibody and the labelled antibody. This is subsequently made insoluble with the help of a carrier-bound antibody which is directed against the Fc$\gamma$ part of the non-labelled soluble antibody. In the case of this process variant, at least the non-labelled, soluble antibody must be an antibody according to the present invention. The labelled antibody is thereby preferably used in excess.

The essence of the present invention is to be seen in that, surprisingly, it is possible to make available for these immunological processes monoclonal antibodies which are directed specifically against FSH and which, therefore, make possible a specific determination of FSH.

Therefore, the present invention also provides monoclonal antibodies against FSH, the cross-reactivity of which with other glycoprotein hormones amounts to less than 3%.

For obtaining the monoclonal antibodies according to the present invention, experimental animals, for example mice, are immunised with FSH. For the immunisation, the immunogen is administered in the usual way, for example in combination with an adjuvant. Preferably, as adjuvant, there is employed aluminium hydroxide, together with *Bordetella pertussis* or Freund's adjuvant. The immunisation preferably takes place over the course of several months with at least four immunisations at 4 to 6 week intervals (intraperitoneal injection).

From the so immunised animals are obtained B-lymphocytes which are fusioned with a permanent myeloma cell line. The fusioning takes place according to the known process of Kohler and Milstein (Nature, 256, 495–497/1976). The primary cultures of hybrid cells thereby formed are cloned in the usual way, for example with the use of a commercially-available cell sorter or by "limiting dilution". In each case, those cultures are further worked up which, in an appropriate test process, for example an enzyme-immuno assay (ELISA process), react positively against FSH and negatively or only to a small extent with the other glycoprotein hormones. Several hybridoma cell lines are thus obtained which produce monoclonal antibodies according to the present invention. These cell lines can be cultured according to known methods and the monoclonal antibodies produced by them are isolated.

As examples of cell lines obtained in this way, there are mentioned:

| | |
|---|---|
| clone 293 | (NCACC 84122002), |
| clone 163 | (NCACC 84122006) and |
| clone 381 | (NCACC 85022205). |

The cell lines have been deposited under the given number at the NCACC depository (National Collection of Animal Cell Cultures).

The so obtained monoclonal antibodies have a very high affinity (affinity constant of the order of magnitude of $>10^8$ l/mol as determined by the method of Scatchard, *Ann. N.Y. Acad. Sci.* 51: 660 (1949)) against FSH and cross-react with other glycoprotein hormones to an extent of less than 3%. Preferred monoclonal antibodies display a cross-reactivity towards other glycoprotein hormones, such as hCG, LH and TSH, of less than 1% and especially of less than 0.1%. For the determination of the affinity and of the cross-reactivity with other hormones, there can be used the processes known for this purpose.

The monoclonal antibodies according to the present invention are outstandingly useful for the specific determination in a sample, for example serum or plasma, of the hormone FSH in the presence of other glycoprotein hormones. For these determination processes, there can be used the monoclonal antibodies as such or fragments hereof which possess the corresponding immunological properties, for example Fab fragments. Therefore, the term "monoclonal antibodies" is to be understood to mean not only the complete antibodies but also the fragments thereof.

The following Examples are given for the purpose of illustrating the present invention:

EXAMPLE 1

Obtaining of monoclonal antibodies against FSH

Balb/c mice, 8–12 weeks old, are immunised intraperitoneally with 100 µg. hFSH (obtainable from Immunex), adsorbed on aluminium hydroxide and *Bordetella pertussis*. After 6 weeks, three further immunisations are carried out at 4 week intervals. In each case, 50 µg. FSH, adsorbed on aluminium hydroxide and *Bordetella pertussis*, are administered intraperitoneally.

About four months after the last immunisation, fusioning is carried out. Four days and three days before fusioning, immunisation is carried out once more intraperitoneally or intravenously with 100 µg. FSH/PBS (phosphate buffered saline).

For the fusioning, with reference to the method described by Galfre (Methods in Enzymology, 73, 3/1981), $10^8$ spleen cells of an immunised mouse are mixed once with $2 \times 10^7$ myeloma cells (P3x63Ag8-653; ATCC-CRL 8375) and subsequently centrifuged (300 g, 4° C.) for 10 minutes. The cells are again washed with BSS (balanced salt solution) and centrifuged at 400 g. The supernatant is removed. The cell sediment is mixed with 1 ml. of a 50% PEG solution (MW 4000, Merck). Thereafter, at ambient temperature, 5 ml. RPMI 1640 medium (RPMI=Rosewell Parker Memory Institute) without foetal calf serum (FCS) and subsequently once more 5 ml. RPMI 1640 medium with 10% FCS, are slowly added dropwise thereto, the mixture is made up to 50 ml. with medium and centrifuged for 10 minutes to 400 g. The sedimented cells are taken up in RPMI 1640 medium containing 10% FCS. In each case, $2 \times 10^5$ spleen cells are seeded on to 24-well cell culture plates (obtainable from Nunc). To each culture are added $1 \times 10^5$ spleen cells or $5 \times 10^4$ peritoneal exudate cells as feed cells. On the following day, hypoxanthine-azaserine selection medium (100 mM hypoxanthine, 1 µg./ml. azaserine) is added thereto.

After about 7–10 days, many clones are already visible. The supernatant of the primary cultures is tested by the ELISA process described in Example 2. Primary cultures which contain antigen-specific antibodies are further cloned with the help of a fluorescence-activated cell sorter on 96-well cell culture plates (obtainable from Nunc). As feed cells, there are used $1 \times 10^4$ peritoneal exudate cells or $2 \times 10^4$ spleen cells per 96-well of the culture.

In this way, there can be isolated, for example, the hybridoma cell lines of clone 293, clone 163 and clone 381 which have been deposited with the NCACC depository (National Collection of Animal Cell Cultures) under the deposit numbers:

| | |
|---|---|
| NCACC 84122002 | (clone 293) |
| NCACC 84122006 | (clone 163) and |
| NCACC 85022205 | (clone 381). |

These cell lines are available to one determined to be entitled thereto by the United States Commissioner of Patents and Trademarks, pursuant to 35 U.S.C. §122, and 37 U.S.C. §1.14.

For the production of ascites, $5 \times 10^6$ hybrid cells are injected intraperitoneally into mice which had previously been pre-treated 1 to 2 times with 0.5 ml. pristane. One to three weeks thereafter, ascites fluid can be obtained from the mice and the antibodies can be isolated therefrom in the usual way. These monoclonal antibodies are directed specifically against FSH and show no or only a slight cross-reactivity with other glycoprotein hormones. In the following, they are designated as MAB 293 (from clone 293), MAB 163 (from clone 163) and MAB 381 (from clone 381).

These monoclonal antibodies belong to the subclass IgGl/K. Their affinity lies above $10^8$ l/mol. For the determination of the affinities, competition curves are determined with the homologous antigen according to the method of Scatchard (Ann. N.Y. Acad. Sci, 51, 660/1949) and evaluated. The measurements necessary therefor are carried out analogously to Example 2.

EXAMPLE 2

Screening test on antibodies against FSH

In order to recognise the presence and specificity of antibodies against FSH in the serum of immunised mice or in the culture supernatant of the hybrid cells or in ascites, an ELISA process is employed as test principle: Microtitre plates are coated with 1 µg. FSH/ml. of coating buffer (0.2M sodium carbonate/bicarbonate; pH 9.3–9.5) at 37° C. overnight and then after-treated for 10 minutes with 0.9% sodium chloride solution and 1% albumin solution and subsequently washed with 0.9% sodium chloride solution. Subsequently, incubation is carried out at 37° C. for one hour with 100 µl. of sample and again washed with 0.9% sodium chloride solution. There follows a further incubation for one hour at 37° C. with 100 to 150 mU/ml. of a sheep anti-mouse-IgG peroxidase conjugate. After a further washing step with 0.9% sodium chloride solution, the peroxidase activity is determined in the usual way (for example with ABTS, 30 minutes at ambient temperature, there being read off the extinction difference, $\Delta mE$ at 405 nm).

The ELISA test can also be carried out as follows:

The microtitre plates are first coated with a sheep anti-mouse-IgG (20–30 µg./ml. coating buffer, one hour to overnight, 37° C.). Thereafter, further treatment is carried out as described above, the sample solution is added and again washed. Finally, incubation is carried out with 250 mU/ml. of an FSH-peroxidase for 1 hour at 37° C. After again washing, the peroxidase activity is determined, for example with ABTS.

EXAMPLE 3

Determination of the cross-reactivity with other glycoprotein hormones

The procedure described in Example 2 is used. The reactivity of FSH is first determined. Then, to the particular monoclonal antibody is, in each case, added the antigen to be tested for cross-reaction (hCG, TSH, LH) in increasing concentration.

The cross-reactions are subsequently calculated according to the following equation:

$$\frac{C(FSH)}{C(\text{cross-reacting antigen})} \times 100 = \% \text{ cross reaction}$$

C = concentration of the antigen which is necessary for the achievement of 50% of the maximum signal.

In the following Table 1 are set out the measured values for MAB 293, MAB 163 and MAB 381:

TABLE 1

Cross-reaction of the monoclonal antibodies MAB 293, MAB 163 and MAB 381 against FSH with hCG, LH and TSH

| glyco-hormone | max. conc. in the serum | conc. range in the test for cross-react. | MAB 293 % cross reaction | MAB 163 % cross reaction | MAB 381 % cross reaction |
|---|---|---|---|---|---|
| hCG (UCB, Belgium) | 200 IU/ml. | 0–250 IU/ml. | <0.1 | <0.1 | <0.1 |
| LH | 400 | 0–12 | <0.1 | <0.1 | <0.1 |

TABLE 1-continued

Cross-reaction of the monoclonal antibodies MAB 293, MAB 163 and MAB 381 against FSH with hCG, LH and TSH

| glyco-hormone | max. conc. in the serum | conc. range in the test for cross-react. | MAB 293 % cross reaction | MAB 163 % cross reaction | MAB 381 % cross reaction |
|---|---|---|---|---|---|
| (UCB, Belgium) | IU/ml. | IU/ml. | | | |
| TSH (Boehringer Mannheim) | 1000 µIU/ml. | 0–9000 µIU/ml. | <0.1 | <0.1 | <0.1 |

EXAMPLE 4

Determination of epitope specificity

A microtitre plate is coated with 10 µg./ml. sheep antibodies against the Fcγ region of a mouse antibody in 0.2M carbonate buffer (pH 9.6) for 2 hours at 37° C. or overnight at 4° C. Thereafter, it is washed with PBS/0.1% Tween 20 (pH 7.35). Subsequently, 100 µl. of a monoclonal antibody (MAB 1, concentration 10 µg./ml.) in incubation buffer (PBS, 0.1% bovine serum albumin (BSA), 0.1% Tween 20) are added thereto and incubated for 2 hours at 37° C.

An FSH peroxidase conjugate (100 mU/ml.) is preincubated overnight with 10 µg./ml. of a second monoclonal antibody (MAB 2) in solution at 4° C.

After the incubation of the plate with MAB 1, excess MAB 1 is removed by washing with PBS-Tween 20. The plate is thereupon after-coated with 1% mouse normal serum in PBS-BSA for 30 minutes at ambient temperature. 100 µl. of the pre-incubated MAB 2/FSH-peroxidase complex are added to the plate and incubated for 2 hours at 37° C. The bound peroxidase activity is made visible with ABTS as substrate. The measured colour intensity is directly proportional to the MAB 2/FSH-peroxidase conjugate bound to MAB 1.

The measurement results found with the various monoclonal antibodies are set out in the following summary, the bound activity being expressed as a percentage of the non-competitively bound FSH-peroxidase activity:

| | MAB 1 | | |
|---|---|---|---|
| | 292 | 163 | 381 |
| MAB 2 | | | |
| 293 | 0 | 0 | 20 |
| 163 | 0 | 0 | 20 |
| 381 | 20 | 20 | 0 |

The results found show that the monoclonal antibody MAB 381 is directed against a different epitope of the antigen FSH than the two antibodies MAB 293 and MAB 163.

EXAMPLE 5

Determination of FSH (A) Preparation of the reagent solutions (1) Substrate buffer:
 15 mM sodium phosphate buffer, pH 7.4
 15 mM sodium chloride
 5 mM EDTA
 0.2% bovine serum albumin, pH 7.4

5 mM o-nitrophenyl galactoside (2) Receptor 1 solution:

As receptor 1, there is employed a monoclonal mouse anti-FSH antibody according to the present invention. The ascites fluid containing this antibody is mixed ad 1.8M with ammonium sulphate. The precipitate is taken up in a buffer of 15 mM sodium phosphate (pH 7.0) and 50 mM sodium chloride. The solution so obtained is subjected to a passage over DEAE-cellulose.

(3) Receptor 3 solution:

As receptor 3, there is also employed a monoclonal mouse anti-FSH antibody according to the present invention which, however, recognises a different antigenic determinant than receptor 1. The ascites fluid containing this antibody is purified as described in (2) above. The complete antibody is split in known manner into the Fab fragment. The Fab fragments obtained are coupled with β-galactosidase according to the method of R. R. Porter (Biochem. J., 73, 119/1959).

(4) Activated receptor 2 solution:

Sheep anti-mouse-Fcγ antiserum is mixed ad 1.8M with ammonium sulphate. The precipitate is taken up in a buffer of 15 mM sodium phosphate (pH 7.0) and 50 mM sodium chloride. The solution so obtained is subjected to a passage over DEAE-cellulose.

(B) Production of reagent carriers (1) Reagent carrier 1:

40 µl. of a solution which contains, per ml.

100 µmol sodium phosphate (pH 7.3, 37° C.),

2 µmol magnesium chloride, 0.9% sodium chloride, 0.5% bovine serum albumin

5 µg. anti-FSH monoclonal antibody from mouse (receptor 1 solution)

100 mU anti-FSH-antibody (mouse) Fab fragment-β-galactosidase conjugate (receptor 3 solution), is applied dropwise to a fleece which consists of a commercial polyester paper. Subsequently, it is dried at ambient temperature. Until used, this fleece is stored at 4° C. and at a relative atmospheric humidity of 20%.

(2) Reagent carrier 2:

Sheep antibodies against the Fcγ part of mouse antibodies (activated receptor 2 solution) are fixed on to a cellulose fleece according to the known cyanogen bromide process (see Federal Republic of Germany patent Specification No. 1768512), whereby, per g. of fibre material, 10 µg. of antibody are provided for the fixing. Uncoupled antibody is removed by washing and the fleece is gently dried at ambient temperature. The so obtained fleece is stored analogously to reagent carrier 1.

The determination with the help of these two reagent carriers 1 and 2 takes place with the use of the device described in Federal Republic of Germany Patent Specification No. 3425008 for carrying out analytical determinations (see FIG. 1 of the accompanying drawings). This describes a rotor insert element for centrifugal automatic analysers comprising a formed body which contains a sample application chamber, which is in connection with a plurality of reagent fields, each of which contains an absorbent material impregnated with a particular reagent, at least one mixing valve chamber and a measurement chamber which together form a sample liquid transport path which leads from radially inwardly to radially further outwardly when the insert element is fixed on the rotor and also has at least one further chamber for the reception of a liquid and a transport path which leads from this chamber to the measurement chamber and is at least partly identical with the sample liquid transport path. The sample liquid transport path thereby leads from a sample application chamber (P) via a chamber (a) filled with absorbent material containing buffer, a chamber (c) and a first valve chamber (VK1) arranged between the chambers (a) and (c), to a second valve chamber (VK2) and from this, via a chamber (d) and via a collection chamber (AK), to a measurement chamber (K). For the reception of a further liquid, there is provided a substrate chamber (PK) formed as pump chamber which is connected via a dosaging device, comprising a dosaging chamber (DK) and capillary (Kap), and an overflow chamber (UK) with a second valve chamber (VK2). FIG. 1 of the accompanying drawings shows schematically the rotor insert element used. The reagent carrier 1 is thereby placed on field c of the disposable insert element and reagent carrier 2 on field d. 40 µl. of sample are thereby pipetted through an opening on the upper edge directly on to field a, the sample being undiluted. 270 µl. of substrate solution are pipetted into chamber PK. By means of an appropriate programme, where high speeds of rotation alternate with stopping, the sample and the substrate solution are then conveyed in the direction of the separation matrix and cuvette.

In the course of the programme, the receptors 1 and 3 are thereby eluted by the sample fluid from field c and the homogeneous mixture is subsequently brought to reaction. The complexes formed are bound to the receptor 2 on field d. The transfer of the sample from field c to field d takes place within a very short period of time.

The substrate solution is divided into portions by the dosaging chamber DK, the first of which serves for washing out excess, non-complexed conjugate.

The β-galactosidase activity bound via complex formation to d is proportional to the amount of FSH contained in the sample. This activity is determined with a further substrate portion, the substrate thereby being reacted in a 5 minute reaction to give coloured products. The colour formed is measured in the cuvette at 410 nm.

A calibration curve is obtained from calibration sera with known FSH contents which cover the range from 0 to 4 ng. FSH/ml. (standardised according to the first IRP Standard for FSH 68/40) and makes possible a sufficiently sensitive measurement of FSH in serum or plasma. On the basis of this calibration curve, there can be determined the unknown content of FSH in body fluids, for example in serum or in a sample.

EXAMPLE 6

Determination of FSH according to the sandwich principle

100 µl. of a solution which contains a monoclonal antibody according to the present invention against FSH in a coating buffer (0.2M sodium carbonate/bicarbonate; pH 9.4) in a concentration of 50 µg./ml. are introduced into each recess of a microtitre plate and incubated for one hour at ambient temperature. Subsequently, it is after-coated with incubation buffer (1% bovine serum albumin, 0.9% sodium chloride) and incubated for 30 minutes at ambient temperature. After washing with wash buffer (0.9% sodium chloride, 0.1% Tween 20), into each recess are placed 100 µl. of sample which contains the FSH to be determined and incubated for 30 minutes at ambient temperature. After again washing with wash buffer, it is charged with 100 μl. of a conjugate of peroxidase (activity 100 mU/ml.) and a further monoclonal antibody according to the present invention but which is directed against another epitope of FSH and incubated for 1 hour at ambient temperature.

For the preparation of the conjugate, there is used horseradish peroxidase (EC 1.11.1.7). The conjugate is prepared by oxidation with periodate and subsequent reduction with boron hydride according to the procedure of P. K. Nakane (M. B. Wilson and P. K. Nakane, in W. Knapp ed. "Immunofluorescence and Related Staining Techniques, 1978, Elsevier/North Holland, Biomedical Press, pages 215-224).

After washing with wash buffer, it is loaded with 100 μl. ABTS substrate solution and, after a one hour colour reaction, the extinction is measured at 405 nm in an ELISA reader (Dynatec).

Figure 2:
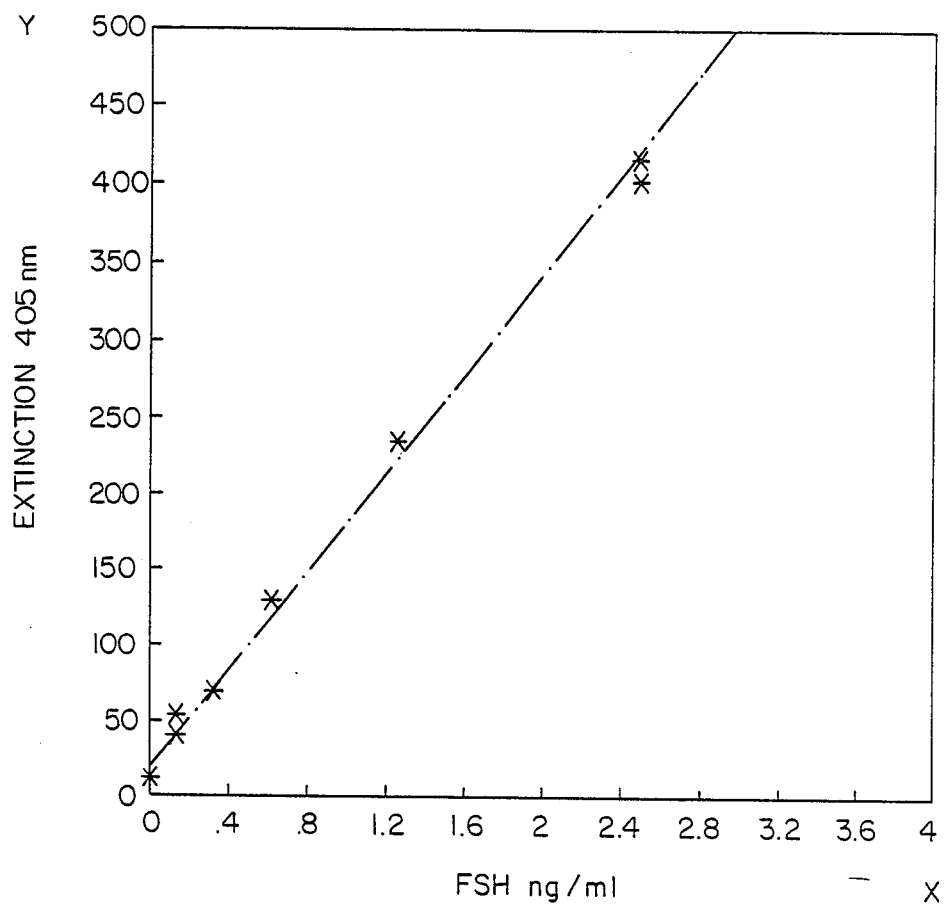

For the production of a calibration curve, in the case of the above-described process, instead of the sample, solutions are used which contain FSH in different, definite concentrations in incubation buffer (see FIG. 2 of the accompanying drawings).

We claim:

1. Hybridoma cell line which produces a monoclonal antibody which specifically binds to follicle stimulating hormone (FSH) and cross-reacts with other glycoprotein hormones to an extent less than 3%.

2. Cell line of claim 1, comprising the cell line identified by National Collection of Animal Cell Culture Number NCACC 84122002.

3. Cell lines of claim 1, comprising the cell line identified by National Collection of Animal Cell Culture Number NCACC 84122006.

4. Cell line of claim 1, comprising the cell line identified by National Collection of Animal Cell Culture Number NCACC 85022205.

5. Monoclonal antibody which specifically binds to follicle stimulating hormone (FSH) and is cross-reactive with other glycoprotein hormones to an extent less than 3%.

6. Monoclonal antibody of claim 5, wherein said monoclonal antibody is cross-reactive to an extent less than 1%.

7. Monoclonal antibody of claim 5, comprising monoclonal antibody MAB 293.

8. Monoclonal antibody of claim 5, comprising monoclonal antibody MAB 163.

9. Monoclonal antibody of claim 5, comprising monoclonal antibody MAB 381.

10. Process for determining the presence of follicle stimulating hormone (FSH) in a sample comprising contacting said sample with at least one monoclonal antibody which specifically binds to FSH and is cross-reactive with other glycoprotein hormones to an extent less than 3% under conditions favoring formation of complexes between said antibody and FSH, and determining the presence of said complexes.

11. Process of claim 10, wherein said monoclonal antibody is cross-reactive with other glycoprotein hormones to an extent less than 1%.

12. Process of claim 10, wherein said monoclonal antibody is selected from the group consisting of MAB 293, MAB 163, and MAB 381.

13. Process of claim 10, wherein said monoclonal antibody is radiolabelled.

14. Process of claim 10, wherein said monoclonal antibody is enzymatically labelled.

15. Process of claim 10, wherein said monoclonal antibody is fluorescently labelled.

16. Process of claim 10, wherein said monoclonal antibody is colorimetrically labelled.

17. Process of claim 10, wherein at least two monoclonal antibodies are used, at least one of said monoclonal antibodies cross-reactive with other glycoprotein hormones to an extent less than 3%.

18. Process of claim 17, comprising sandwich immunoassay.

19. Process of claim 18, comprising forward sandwich immunoassay.

20. Process of claim 18, comprising simultaneous sandwich immunoassay.

21. Process of claim 18, comprising reverse sandwich immunoassay.

22. Process of claim 17, wherein said monoclonal antibodies are selected from the group consisting of MAB 293, MAB 163, and MAB 381.

23. Reagent useful in determining the presence of follicle stimulating hormone (FSH) comprising at least one monoclonal antibody which specifically binds to FSH and cross-reacts with other glycoprotein hormones to an extent less than 3%.

24. Reagent of claim 23, wherein said monoclonal antibody is cross-reactive with other glycoprotein hormones to an extent less than 1%.

25. Reagent of claim 23, wherein said monoclonal antibody is selected from the group consisting of MAB 293, MAB 163, and MAB 381.

26. Reagent of claim 23, comprising at least two monoclonal antibodies at least one of which cross-reacts with other glycoprotein hormones to an extent less than 3%.

27. Reagent of claim 26, wherein at least one of said monoclonal antibodies is selected from the group consisting of MAB 293, MAB 163, and MAB 381.

28. A kit useful in determining the presence of follicle stimulating hormone (FSH) comprising separate components of reagents, at least one of said components being a monoclonal antibody which specifically binds to FSH and cross-reacts with other glycoprotein hormones to an extent less than 3%.

29. Kit of claim 28, wherein said antibody cross-reacts with other glycoprotein hormones to an extent less than 1%.

30. Kit of claim 28, wherein said antibody is selected from the group consisting of MAB 293, MAB 163, and MAB 381.

31. Kit of claim 28, comprising at least two monoclonal antibodies specific for FSH, at least one of which is cross-reactive to an extent less than 3%.

32. Kit of claim 31, wherein at least one of said monoclonal antibodies is selected from the group consisting of MAB 293, MAB 163, and MAB 381.

* * * * *